United States Patent [19]

Arnold et al.

[11] 4,209,695
[45] Jun. 24, 1980

[54] DETECTION OF IMPURITIES IN FLUID FLOWING IN REFINERY PIPELINE OR OIL PRODUCTION OPERATIONS USING NUCLEAR TECHNIQUES

[75] Inventors: Dan M. Arnold; Harold E. Peelman; Obie M. Langford; Hans J. Paap; Irwin R. Supernaw, all of Houston, Tex.

[73] Assignee: Texaco Inc., White Plains, N.Y.

[21] Appl. No.: 872,981

[22] Filed: Jan. 27, 1978

Related U.S. Application Data

[63] Continuation-in-part of Ser. No. 748,072, Dec. 6, 1976, abandoned.

[51] Int. Cl.² ............................................. G01V 5/00
[52] U.S. Cl. .................................. 250/270; 250/261; 250/301; 250/432 R
[58] Field of Search ........... 250/356, 270, 301, 432 R, 250/261

[56] References Cited

U.S. PATENT DOCUMENTS

| Re. 24,383 | 10/1957 | McKay | 250/270 |
| 3,108,188 | 10/1963 | Dewan et al. | 250/270 |
| 3,247,381 | 4/1966 | Caldwell et al. | 250/270 |
| 3,829,686 | 8/1974 | Schultz et al. | 250/270 |

Primary Examiner—Alfred E. Smith
Assistant Examiner—Carolyn E. Fields
Attorney, Agent, or Firm—Carl G. Ries; Thomas H. Whaley; William J. Beard

[57] ABSTRACT

Fluid in a pipeline or container at a refinery or at any of various petroleum producing operations is bombarded with neutrons, and high energy gamma rays resulting from capture of thermal neutrons are detected. The spectra of the detected gamma rays are then analyzed to determine the concentration of the element chlorine, which gives an indication of the presence and concentration of salt water in the fluid. The concentration of sulfur and the percentage gas in the fluid may be determined simultaneously with the concentration of chlorine.

23 Claims, 8 Drawing Figures

TYPICAL $(n,\gamma)$ SPECTRUM
CRUDE OIL WITH CHLORINE

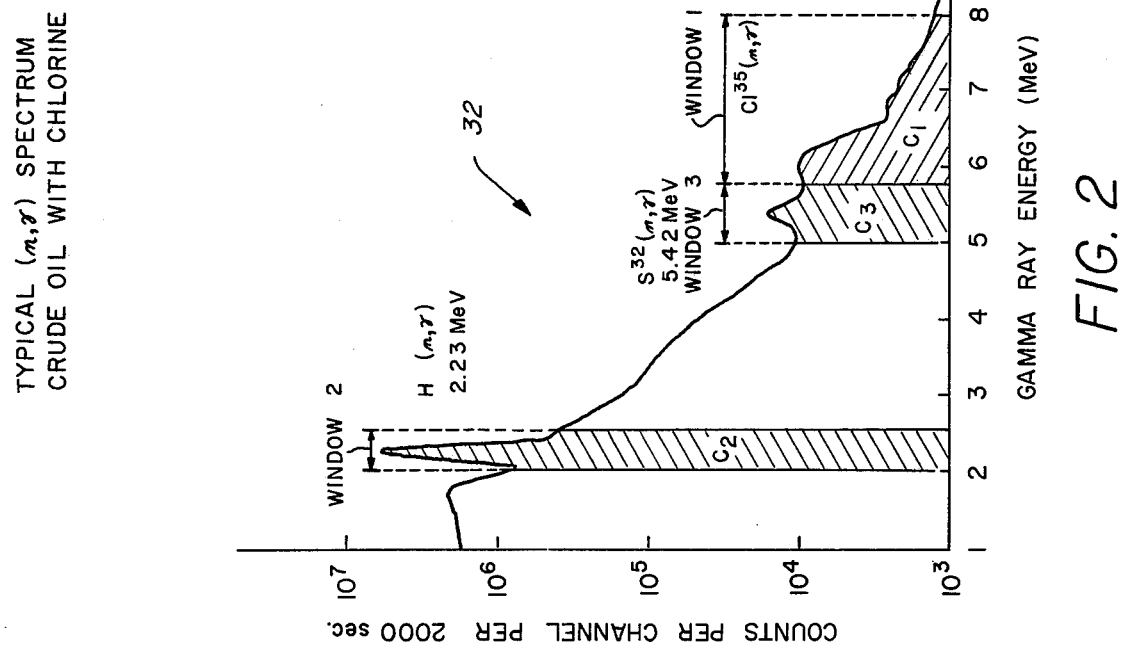
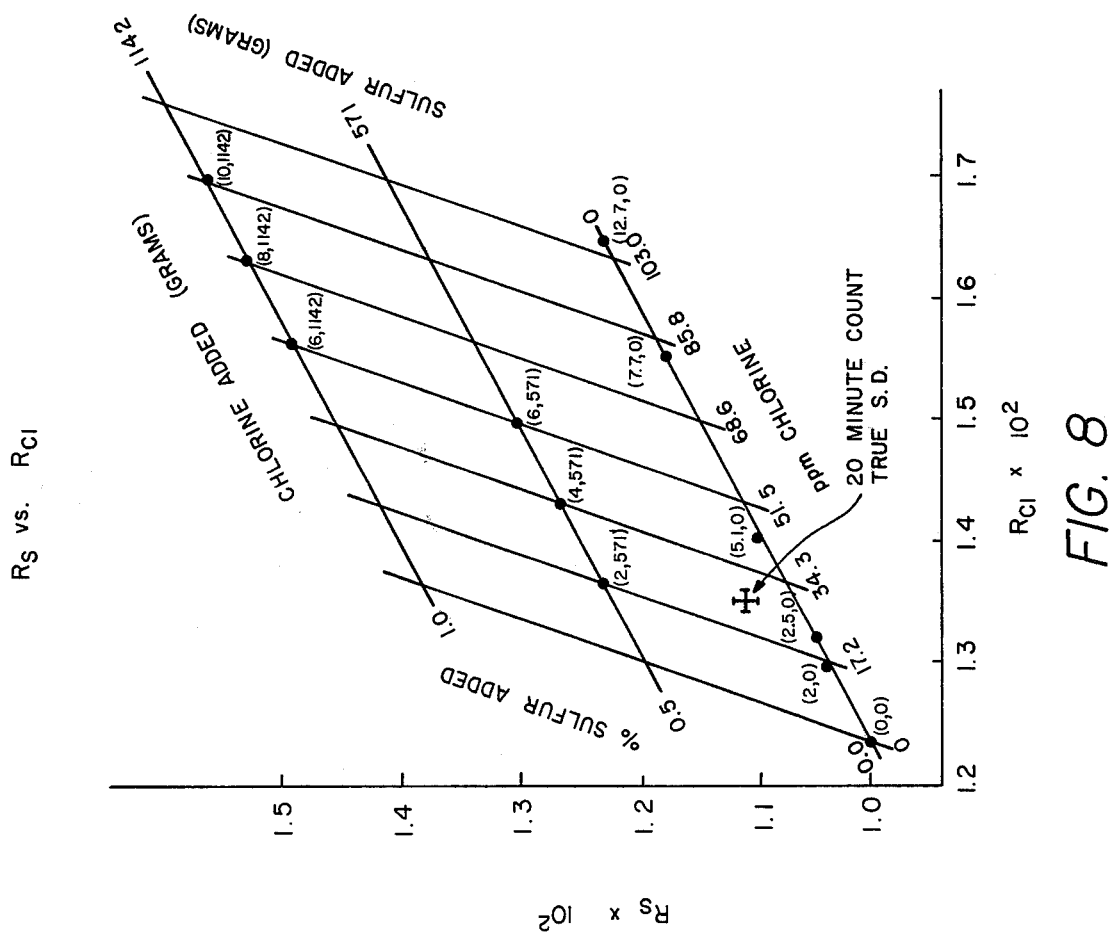

DETECTION OF IMPURITIES IN FLUID FLOWING IN REFINERY PIPELINE OR OIL PRODUCTION OPERATIONS USING NUCLEAR TECHNIQUES

This application is a continuation-in-part of application Ser. No. 748,072 filed Dec. 6, 1976, now abandoned.

BACKGROUND OF THE INVENTION

1. Field of Invention

The present invention relates to nuclear technique for detecting impurities such as salt water and sulfur in petroleum refining and producing operations.

2. Description of Prior Art

Petroleum products often contain small concentrations of undesirable impurities, such as chlorine, sulfur and other elements. For example, even relatively small concentrations of salt water in crude oil can often cause major problems during refining operations. The amount of sulfur in petroleum or fuel oil must be closely monitored for processing and environmental reasons.

A recent article in *Analytical Chemistry*, Volume 46, Number 9, August, 1974, page 1223 and following, deals with determining the amount of sulfur in oil using neutron capture gamma ray spectroscopy. However, it has been found with the present invention that for crude oil of varying and unknown chlorine content, the sulfur readings are varied due to the varying chlorine content. The isotope $^{32}S$, upon capture of thermal neutrons, emits relatively low intensity 8.64, 7.78, 7.42, 7.19, 6.64 and 5.97 MeV gamma radiation in addition to the relatively intense 5.42 MeV radiation. The isotope $^{35}Cl$, upon capture of thermal neutrons, emits 7.79, 7.42, 6.64 and 6.11 MeV gamma radiation. The second and first escape peaks of the 6.64 and 6.11 MeV chlorine capture gamma radiation fall at energies 5.62 and 5.60 MeV, respectively. These escape peaks essentially overlap the primary sulfur capture peak at 5.43 MeV. Due to these overlapping energy peaks, unless the chlorine level in a sample were known and constant, sulfur readings obtained with this prior art technique were not accurate. However, the salt water (and thus chlorine) content of crude oil varies from well to well as well as during the production life of a well for a number of reasons. So far as is known, the only way prior to the present invention to determine chlorine content of crude oil was by chemical analysis.

SUMMARY OF THE INVENTION

Briefly, the present invention relates to a new and improved method and apparatus for determining the presence of chlorine in a fluid conduit. The fluid may be crude oil at a wellhead, loading dock or other location, or refined product, feed stock or waste water to dispose of at a refinery.

The fluid is bombarded with fast neutrons from a neutron source which are slowed down and thereafter engage in thermal neutron capture reactions with materials in the fluid, giving rise to thermal neutron capture gamma rays. The energy spectra of the thermal neutron capture gamma rays are obtained, from which a measure of the concentration of chlorine in the fluid may be ascertained. If the salinity of the salt water is known, the concentration of salt water within the fluid is accordingly determined. Alternatively, since substantially all the chlorine in fluids being sampled is present as sodium chloride, the measure of the relative presence of chlorine is in itself a measure of the presence of salt water.

In further aspects of the present invention, the concentration of sulfur is determined simultaneously with the concentration of chlorine. Also, if the fluid contains a gas homogeneously mixed therein, the percentage of gas or gas oil ratio (GOR) may be determined according to the present invention.

BRIEF DESCRIPTION OF THE DRAWINGS

FIG. 2 is a graphical illustration of a typical thermal neutron capture gamma ray spectrum for crude oil;

FIG. 8 is a graph by which the chlorine and sulfur content of a fluid are simultaneously determined for a fluid as a function of the ratio of chlorine neutron capture gamma ray count and sulfur neutron capture gamma ray count, respectively, from the fluid to the hydrogen neutron capture gamma ray count from the fluid.

DESCRIPTION OF THE PREFERRED EMBODIMENT

Figure 1:
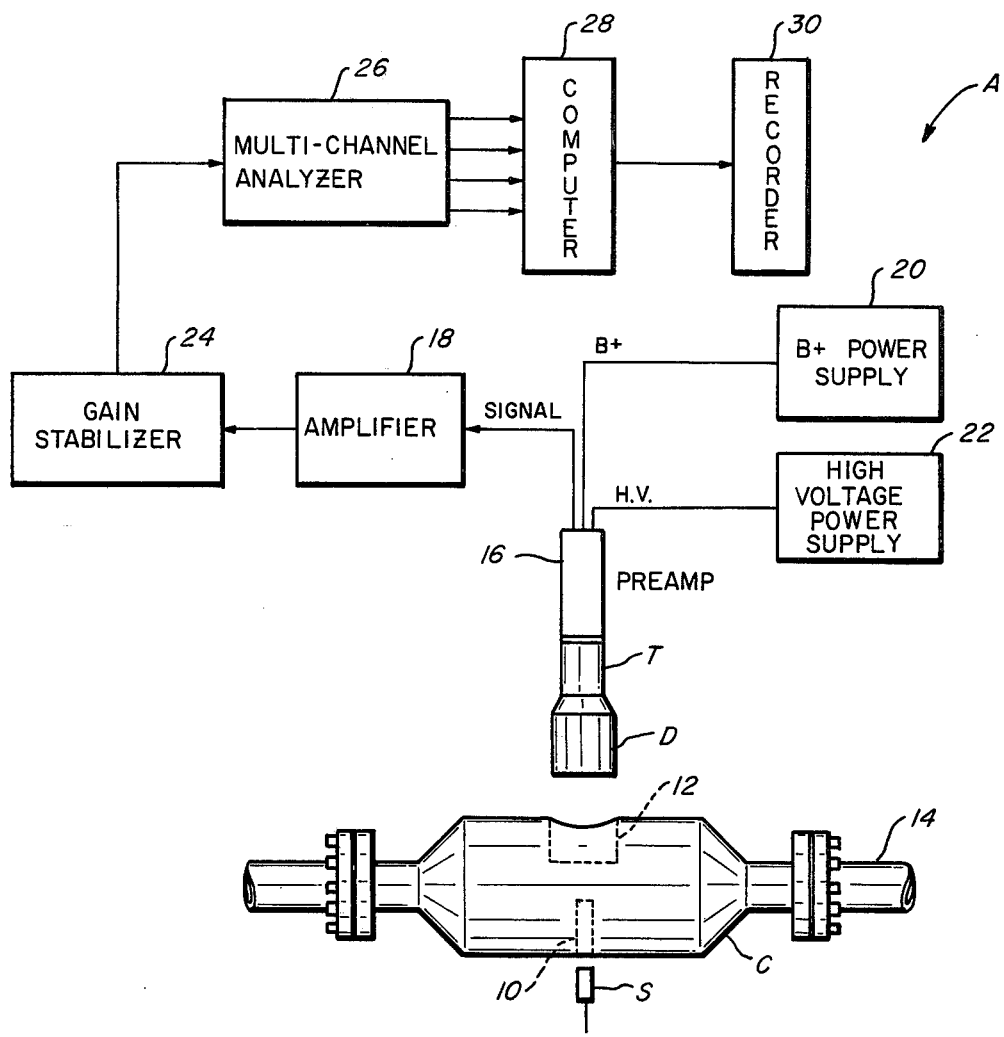
FIGS. 1 and 3 are schematic block diagrams of apparatus according to the present invention.

Relatively small concentrations of salt water in crude oil can often cause major problems in the crude oil refining process. The present invention relates to the detection in a flowing crude oil stream or other petroleum conduit of concentrations of chlorine as low as several parts per million with statistical accuracies of ±15 percent or better. The present invention is based upon the bombardment or irradiation of a flowing stream of crude oil with neutrons and the detection of gamma radiation emitted by the element chlorine upon capture of thermal neutrons. For a given thermal neutron flux, the yield of chlorine capture radiation is proportional to the concentration of chlorine in the flowing stream of crude oil. If it is known or assumed that all chlorine is in the form of NaCl and if the water salinity is known, then the intensity of chlorine capture radiation is a direct indication of salt water concentration.

Gamma radiation resulting from thermal capture (n,γ) reactions is "prompt" in the sense that it is emitted within microseconds after the capture event. This is in contrast to "delayed" gamma radiation resulting from "activation" type reactions which is emitted from milliseconds to years after the reaction. Since thermal neutron capture radiation is almost instantaneous, the velocity and volume flow rate of the crude oil stream do not affect the measurement. Another advantage of the present invention is that since thermal neutrons are required, a chemical source rather than an evacuated envelope accelerator type neutron generator source can be used. Chemical sources are relatively inexpensive and, of course, require no associated electronics or maintenance.

THEORY AND SENSITIVITY CALCULATIONS

The counts C recorded by a gamma ray detector during time T (seconds) is given by the equation $$C = E B N \sigma \phi T \qquad (1)$$

where
- E = the efficiency of the detector
- B = the branching ratio of the counted gamma radiation
- N = the nuclear density of the isotope of interest
- $\sigma$ = the capture cross section for the reaction of interest (cm$^2$)
- $\phi$ = the thermal neutron flux (neutrons/cm$^2$–sec)

The detector efficiency term E can be expressed as $$E = K b \epsilon f \qquad (2)$$

where
- K = a constant depending upon the source-detector geometry
- $\epsilon$ = total efficiency of the detector to the counted gamma radiation
- b = the fraction correction for the absorption of gamma radiation within the sample
- f = the peak to total ratio for the gamma radiation of interest For the Cl$^{35}$(n,$\gamma$) reaction, $\sigma_{Cl}$ = 33.6 barns. The nuclear density $N_{Cl}$ is given by the equation $$N_{Cl} = (P_{Cl} I_{Cl\text{-}35} Q)/(A_{Cl} \cdot 100) = P_{Cl} Q \, 2.15 \cdot 10^{-4} \qquad (3)$$

where
- $P_{Cl}$ = percent by weight of elemental chlorine in the fluid
- $I_{Cl\text{-}35}$ = isotopic fraction of Cl$^{35}$ = 0.755
- Q = Avogadro's number
- $A_{Cl}$ = atomic weight of Cl$^{35}$ = 35

The gamma radiation of interest for chlorine are encompassed within Window 1 (FIG. 2) and their MeV levels along with their corresponding branching ratios B are

| (MeV) Gamma ray energy | B |
|---|---|
| 7.79 | 0.078 |
| 7.42 | 0.140 |
| 6.64 | 0.144 |
| 6.11 | 0.214 |
|  | $\Sigma$ = 0.576 |

All of the above gamma radiations in Window 1 will be counted so that the sum of branching ratios $$B_{Cl} = 0.576 \qquad (4)$$

will be used in Equation (1) to compute $C_{Cl}$.

For a 5" (diameter) × 5" NaI(Tl) cylindrical crystal, the $\epsilon \cong 1.4$ for counted gamma radiation in the 5.75–8.0 MeV range and since this range contains not only photo but escape peaks, f ∼ 0.8. Therefore $$(\epsilon f)_{Cl} = 1.12 \qquad (5)$$

Substituting Equations (2) through (5) into Equation (1) and subscripting C to designate the Cl$^{35}$(n,$\gamma$) reaction yields $$\begin{aligned} C_{Cl} &= (1.12\, K_{Cl} b_{Cl}) \cdot 0.576 \cdot (2.15 \cdot 10^{-4} P_{Cl} Q) \cdot 33.6 \cdot \phi_{Cl} \cdot T_{Cl} \\ &= 0.466\, P_{Cl} Q\, \phi_{Cl}\, T_{Cl}\, K_{Cl}\, b_{Cl} \cdot 10^{-2} \end{aligned} \qquad (6)$$

The prior art article discussed above has measured sulfur content in crude oil using the S$^{32}$(n,$\gamma$) reaction. For S$^{32}$(n,$\gamma$) $\sigma_S$ = 0.51 barns. The nuclear density $N_S$ is given by the equation $$N_S = (P_S I_{S\text{-}32} Q)/(A_S \cdot 100) = P_S Q\, 2.95 \cdot 10^{-4} \qquad (7)$$

where
- $P_S$ = percent by weight of elemental sulfur within the oil
- $I_{S\text{-}32}$ = isotopic fraction of S$^{32}$ = 0.95
- Q = Avogadro's number
- $A_S$ = atomic weight of S$^{32}$ = 32

The predominant gamma radiation of interest from the S$^{32}$(n,$\gamma$) reaction is 5.42 MeV with $$B_S = 0.42 \qquad (8)$$

For the technique used in this article using a 3"×3" NaI(Tl) detector $$(\epsilon f)_S = 0.04 \qquad (9)$$

Substituting Equations (2), (7), (8) and (9) into (1) and subscripting C to designate the S$^{32}$(n,$\gamma$) reaction yields $$\begin{aligned} C_S &= (.04\, K_S b_S) \cdot 0.42 \cdot (2.95 \cdot 10^{-4} P_S Q) \cdot 0.51 \cdot \phi_S \cdot T \\ &= 2.52 \cdot 10^{-6}\, P_S Q\, \phi_S\, T_S\, K_S\, b_S \end{aligned} \qquad (10)$$

From Equations (6) and (10), we have $$C_{Cl} = 1.844 \cdot 10^3\, C_S\, \frac{P_{Cl} \phi_{Cl} T_{Cl} K_{Cl} b_{Cl}}{P_S \phi_S T_S K_S b_S} \qquad (11)$$

If a geometry similar to that in FIG. 1 of the prior art article were used to measure the chlorine content in crude oil, the geometric factors $$K_{Cl} b_{Cl} = K_S b_S \qquad (12)$$

Also referring to the results of the prior art reference, for a controlled sample it was found that for $P_S$ = 1% and $T_S$ = 2000 seconds (33.3 minutes), $C_S$ = 763 counts using a Cf$^{252}$ source emitting 5·10$^5$ neutrons per second. If the chlorine measurement is made using a source emitting 5·10$^7$ neutrons per second, $$\phi_{Cl}/\phi_S = 10^2 \qquad (13)$$

Substituting the above values from this article along with Equations (12) and (13) into Equation (11) yields $$C_{Cl} = 7.03 \times 10^4\, P_{Cl} T_{Cl} \qquad (14)$$

which relates the counts recorded in a 5.75–8.0 MeV window resulting from the Cl$^{35}$(n,$\gamma$) reaction to the percent (by weight) of elemental chlorine in the crude oil for a counting time $T_{Cl}$. In the prior art reference, it was estimated that the $C_B$, the background recorded in the energy window 5.75 to 8.0 MeV is approximately 37 counts per second.

FIG. 1 shows an apparatus A according to the present invention with a neutron source S and a detector D mounted in suitable sockets 10 and 12, respectively, of a counting chamber C mounted in a crude oil flow line 14. The detector D is preferably a 5"×5" NaI(Tl) cylindrical crystal coupled to a photomultiplier tube T. The source S shown is a $Cf^{252}$ neutron source emitting $5 \times 10^7$ neutrons per second, although it should be understood that a different source material, such as actinium-beryllium or americium-beryllium could be used, if desired.

The chamber C preferably should be constructed of some material which contains no elements producing appreciable capture gamma radiation above 5.0 MeV. Aluminum or certain fiberglass-epoxy materials would be suitable, although iron, which produces 9.30 and 7.64 MeV gamma radiation through (n,γ) reactions, should be avoided. It should be noted that the chamber C is designed such that the detector D and source S are physically isolated in the sockets 10 and 12 from the crude oil. This eliminates the possibility of contaminating the crude oil if the source S should leak and also permits the detector D and source S to be removed without interrupting the flow of crude oil.

The physical shape of the chamber C is not critical as long as the source S and detector D are surrounded by at least several inches of fluid. In certain situations it might be desirable to coat the inside of the chamber C with a material of high thermal neutron cross capture cross section, such as boron. This would reduce the thermal neutron interactions with the walls of the chamber and also prevent the escape from the chamber of thermal netrons that might react with elements outside the chamber producing additional "background" radiation. Boron (boron carbide mixed with epoxy resin) would be ideal for this application since it has a large thermal neutron capture cross section ($\sigma=775$ barns) and a capture reaction which produces no radiation above 5.0 MeV.

The detector D produces scintillations or discrete flashes of light whenever gamma rays pass therethrough, while the photomultiplier tube T generates in response to each such scintillation a voltage pulse proportional to the intensity of the scintillation. A conventional preamplifier circuit 16 amplifies the pulses from the photomultiplier tube T and furnishes the amplifier pulses to a further amplifier stage 18. A B+ power supply 20 is provided for the preamplifier 16, and a high voltage power supply 22 is provided for the photomultiplier tube T.

The output pulses from the amplifier 18 are furnished to a gain stabilizer circuit 24 which is calibrated to respond to the energy level of a selected reference peak in the gamma ray energy spectrum, such as the 2.23 MeV energy peak of hydrogen in Window 2 (FIG. 2). It should be understood, however, that other gamma ray energy peaks may be used for gain stabilization, if desired. The gain stabilizer circuit 24 is an automatic gain control circuit which responds to energy level of pulses at the calibrated peak level and adjusts the gain of all energy level pulses from the photomultiplier tube T to compensate for gain shift or variations in tube T and other circuitry of the apparatus of the present invention due to power supply voltage fluctuation and/or temperature effects.

The output pulses from gain stabilizer circuit 24 are supplied to a pulse height or multi-channel analyzer 26. The pulse height analyzer 26 may be of conventional design as known in the art and having, for example, four or more channels or energy divisions corresponding to quantizations or energy ranges of the pulse heights of the input pulses, if desired. The pulse height analyzer 26 functions to sort and accumulate a running total of the incoming pulses into a plurality of storage locations or channels based on the height of the incoming pulses which, it will be recalled, is directly related to the energy of the gamma rays causing the pulse. The output of the pulse height analyzer 26 in the case of the present invention consists of count pulses occurring in each of three energy ranges or windows as depicted in FIG. 2. It should also be understood the three appropriately biased single channel analyzers may be used in place of the multi-channel 26, if desired.

The output from the pulse height analyzer 26 may be stored on a suitable memory device for subsequent processing, or alternatively, is supplied directly over an appropriate number of lines to a computer 28, which obtains from the number of chlorine counts, and the length of time for such count, a measure of the concentration of chlorine or salt water in the fluid in the line 14, in a manner to be set forth. Further, the computer 28 may also simultaneously determine from the output of analyzer 26 a measure of the concentration of sulfur in the fluid in line 14, and the percentage of gas in such fluid. The results of such computations may be stored or displayed, as desired with a recorder 30 or other suitable display device.

FIG. 2 shows a typical capture gamma ray spectrum 32 recorded using the equipment of FIG. 1 for a stream of crude oil containing small amounts of chlorine and sulfur. The intense peak of 2.23 MeV results from the capture of thermal neutrons by hydrogen in the crude oil and is used, as set forth above, as an energy reference peak by the gain stabilizer circuit of FIG. 1. FIG. 2 also shows the energy settings of the multi-channel analyzer 26. The first setting, identified as "Window 1", extends from 5.75 to 8.0 MeV and includes photoelectric and escape peaks from the 7.79, 7.42, 6.64 and 6.11 MeV radiation from the $Cl^{35}$ (n,γ) $Cl^{36}$ reaction as well as the 7.78, 7.42, 7.19, 6.64 and 5.97 MeV peaks from sulfur. The second setting, identified as Window 2, extends from 2.00 to 2.50 MeV and includes the 2.23 MeV hydrogen capture peak. The third setting, identified as Window 3, extends from 5.00 to 5.75 MeV and includes the 5.42 MeV sulfur capture peak.

DETERMINATION OF CHLORINE CONTENT

A. No Free Gas in the Crude Oil

If it is assumed that there is no free gas in the flowing stream of crude oil, the counts recorded in window 1, $C_1$, for a count time T is given by the Equation $$C_1 = C_{Cl} + C_1{}^B \tag{17}$$

where
$C_{Cl}$ = counts due only to the $Cl^{35}(n,\gamma)Cl^{36}$ reaction
$C_1{}^B$ = the background counts in Window 1 due to all gamma radiation other than that from the chlorine capture reaction $C_{Cl}$ can be expressed as $$C_{Cl} = P_{Cl} K_{CL}' T \tag{18}$$

where
- $P_{Cl}$ = the percent (by weight) of element chlorine contained in the crude oil
- $K'_{Cl}$ = a calibration constant depending upon the source strength, source-detector spacing, dedetector efficiency, and geometry of the counting chamber
- $T$ = the count time in seconds Substituting Equation (18) into Equation (17) and solving for $P_{Cl}$ yields (the chlorine concentration)

$$P_{Cl} = \left(\frac{C_1}{T} - \frac{C_1^B}{T}\right)/K'_{Cl} \qquad (19)$$

Figure 6:
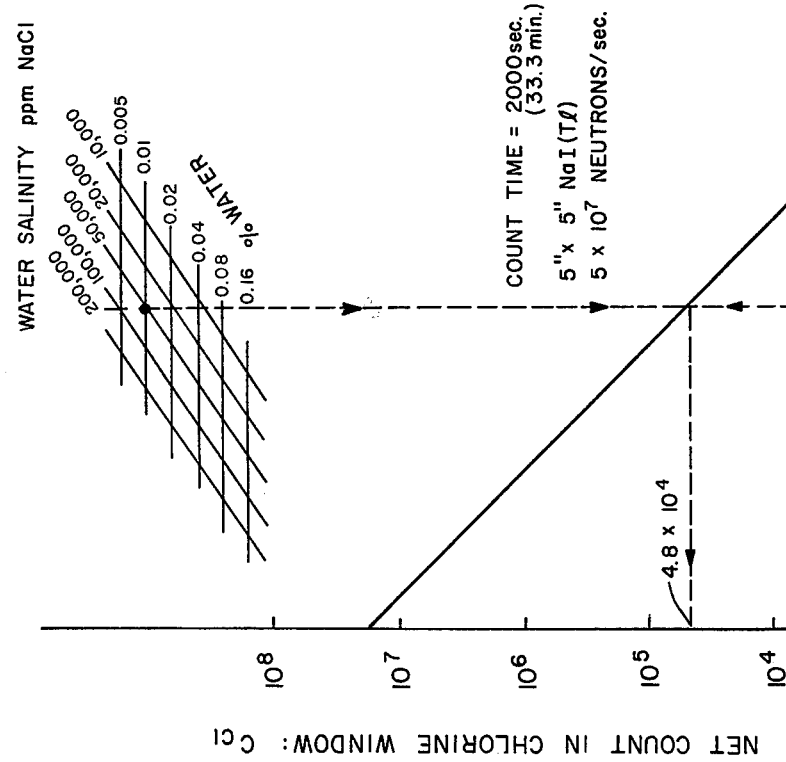
FIG. 6 is a further graphical illustration of net counts of chlorine neutron capture gamma rays as a function of percent chlorine (chlorine concentration) in a fluid obtained with the present invention.

Theoretical Cl detection sensitivity of the apparatus A is summarized in FIG. 6 which shows a plot of $C_{Cl}$ versus $P_{Cl}$ from Equation (14) using a count time $T = 2000$ seconds and $K'_{Cl} = 7.03 \times 10^4$. The grid at the top of the plot can be used to determine $C_{Cl}$ as a function of percent water cut and the salinity of the water in ppm NaCl. The use of FIG. 6 can best be illustrated by the following examples:

Percent water in oil flow = 0.01%
Salinity of water = 50,000 ppm NaCl

This concentration of water and salinity corresponds to a concentration (by weight) of 0.0000303% element chlorine and will produce ($C_{Cl} - 4.8 \times 10^4$ net counts for a count time $T = 2000$ seconds (33.3 minutes).

It is now of interest to determine the statistical accuracy to which chlorine concentration can be measured. The percent standard deviation SD of the measured count $C_{Cl}$ is given by the equation $$SD = [(C_{CL} + [2 \cdot C_B T_{CL}])^{\frac{1}{2}}/C_{CL}] \times 100 \qquad (20)$$

where $C_B$ is the background count rate in the 5.75 to 8.0 MeV window in counts per second. It was stated earlier that $C_B$ was estimated to be 37 counts per second for a $3'' \times 3''$ NaI(Tl) detector and a $Cf^{252}$ source emitting $5 \times 10^5$ neutrons/second. For a $5'' \times 5''$ NaI(Tl) detector, a $5 \cdot 10^7$ neutron/second source, and $T_{Cl} = 2000$ seconds, the quantity $$2 \cdot C_B \cdot T_{Cl} = 2 \cdot 37 \cdot 2000 \, (\epsilon_5 \times 5/\epsilon_3 \times 3) \cdot 10^2$$
$$= 2 \cdot 37 \cdot 2000 \, (1.4/0.4) \cdot 10^2$$
$$= 5.19 \cdot 10^7$$

and Equation (20) reduces to $$SD = [(C_{Cl} + 5.19 \cdot 10^7)^{\frac{1}{2}}/C_{Cl}] \times 100 \qquad (21)$$

Figure 7:
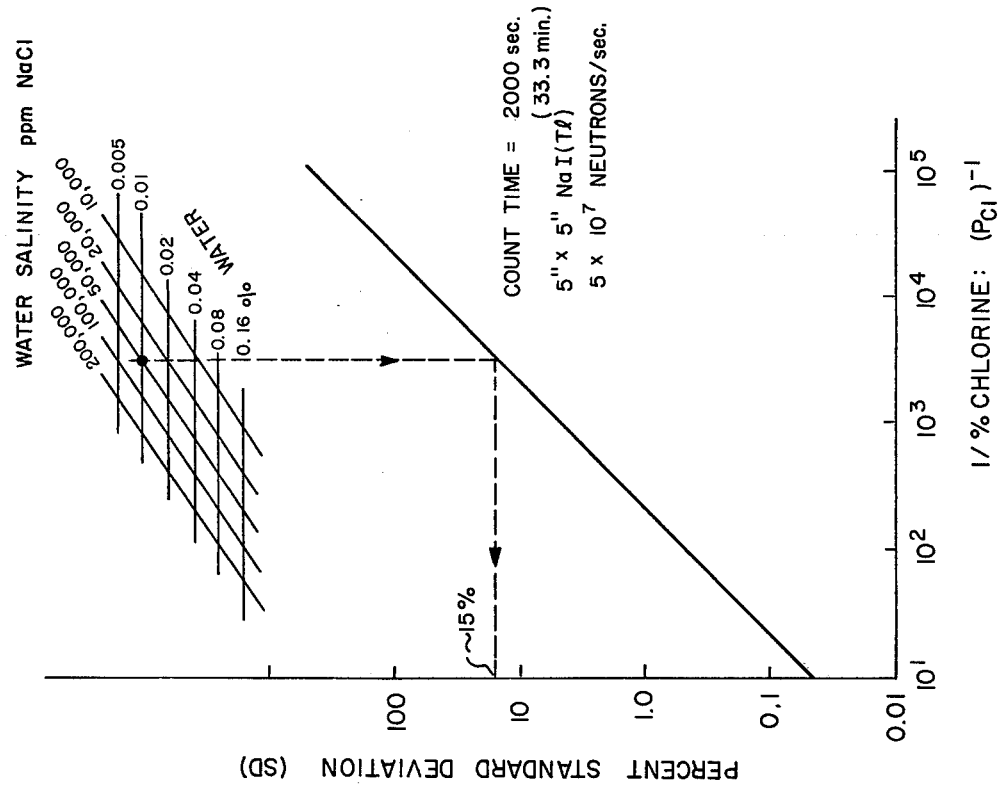
FIG. 7 is a graphical illustration of percent standard deviation of results of the present invention as a function of percent chlorine in a fluid.

FIG. 7 shows a plot of SD from Equation (21) using Equation (14) to relate $C_{Cl}$ to $P_{Cl}^{-1}$ with the percent water cut-salinity grid again included at the top of the plot. Again using the example of 0.01% water cut at a salinity of 50,000 ppm NaCl, it can be seen from FIG. 7 that the chlorine concentration can be measured to a standard deviation of ±15 percent.

B. Free Gas in the Flowing Stream of Crude Oil

If a homogeneous mixture of gas is present in the flowing stream of crude oil, $C_1$ is now given by the Equation $$C_1 = (C_{Cl} + C_1^B) \cdot G(P_G) \qquad (22)$$
$$= (K_{Cl}P_{Cl}T + C_1^B) \cdot G(P_G) \qquad (22a)$$

where $G(P_G)$ is a term dependent upon the hydrogen content of the crude oil-gas mixture which is, in turn, dependent upon $P_G$, the percent gas content of the crude oil. Likewise, the total counts recorded in window 2, $C_2$, is given by the Equation $$C_2 = (C_H + C_2^B) \cdot G(P_G) \qquad (23)$$

where
- $C_H$ = count rate in the Window 2 due to $H(N,\gamma)^2H$ activity
- $C_2^B$ = the background counts in window 2 due to gamma radiation other than that resulting from neutron capture in hydrogen Solving Equations (22a) and (23) for $P_{Cl}$ yields (the chlorine concentration)

$$P_{Cl} = \frac{1}{K_{Cl}} \left[ \frac{C_1}{C_2} \frac{(C_H + C_2^B)}{T} - \frac{C_1^B}{T} \right] \qquad (24)$$

where $C_1/C_2$ is the ratio of gross counts recorded in window 1 to window 2 during a count time T. The remaining terms on the right hand side of Equation (24) are determined when the system is calibrated. Specifically, $C_1^B/T$ is determined by filling the chamber C with crude oil containing no free gas and no chlorine and recording the gross count in window 1 (estimated to be 37 counts per second, as set forth above)

$(C_H + C_2^B)/T$ is also the gross count rate recorded in window 2 with the counting chamber filled with crude oil containing no free gas and no chlorine $K_{Cl}$ is determined by (a) filling the count chamber with crude oil containing no free gas and a known concentration $P_{Cl}$ of chlorine, (b) recording $C_1$ for a time T and (c)$_B$ solving equation (19) for $K_{Cl}$ using $C_1$ as determined above.

It should be noted that Equation (24) does not contain the gas term $G(P_G)$ and is, therefore, independent of the amount of free gas in the fluid.

Subtracting Equation (22) from Equation (23) and solving for $G(P_G)$ yields $$G(P_G) = [C_2 - C_1] [(C_H + C_2^B) - (K_{Cl}P_{Cl}T + C_1^B)] \qquad (25)$$

where
- $(C_2 - C_1)$ is the difference in gross counts recorded in windows 2 and 1, respectively, for time T
- $(C_H + C_2^B)$ is predetermined in the calibration procedure above
- $K_{Cl}$ and $C_1^B$ are also predetermined in the calibration procedure above
- $P_{Cl}$ (the chlorine concentration) is determined from equation (24)

As mentioned earlier, $G(P_G)$ is indicative of the percentage gas content of the flowing stream of crude oil, if the free gas is homogeneously mixed in the fluid stream.

SIMULTANEOUS MEASUREMENT OF CHLORINE AND SULFUR CONTENT

With the present invention, it has also been found possible to determine the effects of variation in the fluid sulfur content upon the chlorine concentration measurement, and the precision to which sulfur concentration in the fluid can be measured. This determination of sulfur content is of particular importance in producing low sulfur fuels in refinery operations. A series of gamma ray spectra was measured after adding known incremental amounts of chlorine (as NaCl) and sulfur (as $H_2SO_4$) to tap water in the counting chamber C using a source-detector spacing of 8". The results are summarized in FIG. 8. $R_{Cl}$, which is the ratio of counts in Window 1 to counts in Window 2, is plotted along the abcissa. $R_S$, the ratio of counts in Window 3 from 5.000 to 5.75 MeV (which includes the 5.42 MeV radiation from thermal neutron capture in sulfur) to the counts in Window 2, is plotted along the ordinate. Data points are denoted by (i, j) where i and j are the grams of chlorine and sulfur, respectively, added to the fluid. Adjacent to each data point is the quantity ($M_{Cl}$, $M_S$) where $M_{Cl}$ and $M_S$ are the masses (in grams) of chlorine and sulfur, respectively, added to the fluid. The grid is constructed by least-squares fitting straight lines through the data and is labeled in grams and ppm or percent of the element added. The concentrations of chlorine and sulfur are also shown in parts per million and percent, respectively. Typical observed standard deviations are shown for $R_{Cl}$ and $R_S$ for a 20 minute count. For this count time, the sulfur concentration can be determined to ±0.08 percent. Results similar to those shown in FIG. 8 can be expected using oil as a base fluid since oil and water have similar neutron moderation properties. Once the $R_S$ versus $R_{Cl}$ grid has been constructed for a given counting chamber, the chlorine and sulfur content of an unknown fluid can be obtained from the measurement of $R_S$ and $R_{Cl}$.

It can be seen that $R_{Cl}$ is affected to some extent by the sulfur content of the fluid. This is a result of the low intensity, high energy capture radiation from sulfur whose primary and escape peaks fall within the "chlorine" Window 1 (FIG. 2). Likewise, it can be seen that $R_S$ is also affected by the chlorine content of the fluid. This results from the escape peaks of the 6.64 and 6.11 MeV chlorine capture radiation that fall within the "sulfur" Window 3. It is apparent, however, that sulfur and chlorine concentrations can be determined uniquely by recording $R_S$ and $R_{Cl}$ simultaneously and using the grid of FIG. 8.

Thus, with the present invention, it is possible to obtain simultaneous measurements of chlorine and sulfur in a flowing stream of crude oil (or waste water), provided three energy windows of interest in the measured gamma ray spectrum are obtained. As set forth above, they are:

| (CHLORINE) | Window 1 | 5.75 MeV to 8.00 MeV |
| (HYDROGEN) | Window 2 | 2.00 MeV to 2.50 MeV |
| (SULFUR) | Window 3 | 5.00 MeV to 5.75 MeV |

Figure 4:
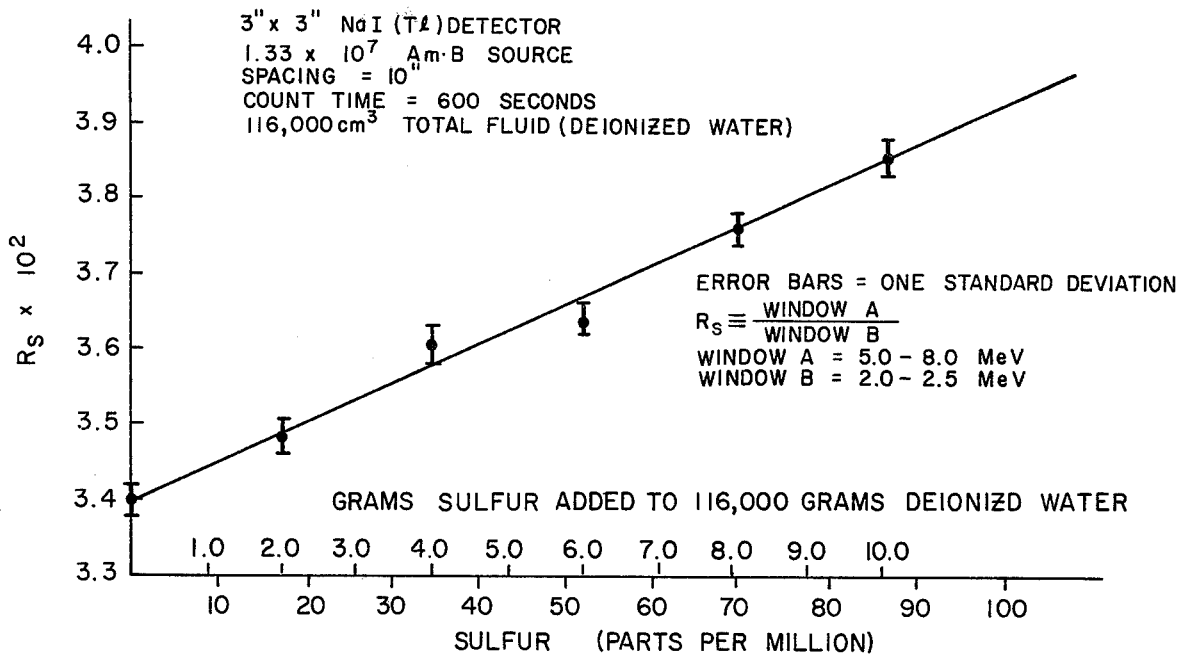
FIG. 4 is a graphical illustration showing the count ratio in sulfur detection energy windows as a function of chlorine concentration.
Figure 5:
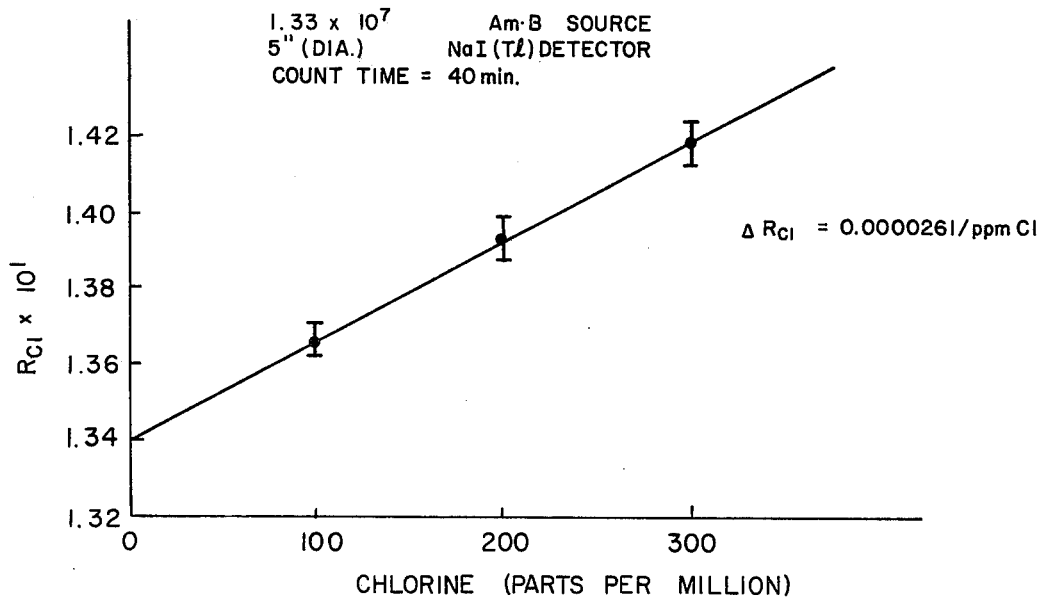
FIG. 5 is a graphical illustration showing the linear response of the count ratio in chlorine detection energy windows as a function of chlorine concentration.

As described above, the ratio of counts recorded in Window 1 to the counts recorded in Window 2, $R_{Cl}$, increases linearly for a given sulfur concentration and (for concentrations of the subject element less than a few percent) with the chlorine content of the fluid and is independent of the hydrogen index or density of the fluid. This is shown in FIG. 5. The ratio of counts recorded in Window 3 to Window 2, $R_s$, also increases linearly (again, for a given chlorine content for concentrations of the subject element less than a few percent) with the sulfur content of the fluid. This is shown in FIG. 4. It is possible, therefore, to measure $R_{Cl}$ and $R_S$ simultaneously and obtain elemental concentrations of both chlorine and sulfur from a plot $R_S$ versus $R_{Cl}$ such as that of FIG. 8.

It should be understood that the techniques described above are not necessarily confined to a counting chamber geometry. In the event that the subject measurement must be made in a flow line without cutting the pipe or without diverting a portion of the stream to a counting chamber as described above, it would still be possible to make an estimation of the chlorine content (albeit not as precise) by locating the source of S and detector D against the pipe 14 on opposite sides of it.

Figure 3:
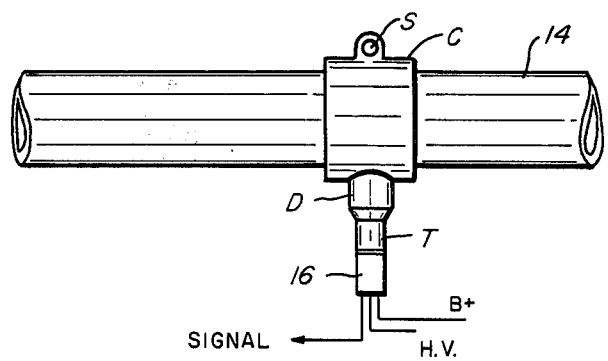

The neutron source S and detector D are mounted on the outside of the existing flow line 14 by means of a suitable clamp device C, or other suitable pipe attachment means, as shown in FIG. 3. The remainder of the apparatus of FIG. 3 corresponds to that of FIG. 1 and thus is not shown. However, this apparatus is connected to the preamplifier 16 and photomultiplier tube T in the manner set forth above for FIG. 1. Measurements have been made indicating that ppm concentrations of chlorine and 0.1 percent concentrations of sulfur can be detected using this "through-pipe" technique of FIG. 3; however, for a given count time, the precision to which the through-pipe measurements can be made is not as good as that obtained using a counting chamber.

From the foregoing, it can be seen that the present invention provides for the simultaneous measurement of chlorine and sulfur and can be used in various producing operations such as (1) Monitoring chlorine and sulfur content at a well head. The chlorine measurement could be used to monitor the water cut of the produced fluid if the salinity of the produced water is known.
(2) Monitor chlorine and sulfur at a loading dock.
(3) Monitor the chlorine and sulfur content of water prior to disposal.

In refining operations, the proposed technique can be used to (1) Monitor sulfur and chlorine in a feed stock.
(2) Monitor sulfur and/or chlorine content of refined products.

Among the primary advantages of the present invention are:

1. Concentrations of chlorine as small as 0.0001 percent (by weight) can be detected in a flowing stream of crude oil.
2. The chlorine concentration measurement is independent of the linear flow velocity or the volume flow rate of the crude oil.
3. The technique is ideally suited for remote, continuous monitoring in the sense that the system requires minimal maintenance and relatively simple electronic equipment.
4. By stabilizing the gain of the gamma ray detector automatically on a suitable peak with gain stabilizer 24, the system will require minimal adjustment and can be operated by unskilled personnel.
5. The system can also give a quantitative indication of the free gas content of the crude oil, (a) if the free gas/liquid mixture is homogeneous and (b) if the linear flow velocities of the liquid and gas phases are the same.

The foregoing disclosure and description of the invention are illustrative and explanatory thereof, and various changes in the size, shape and materials, as well as in the details of the illustrated construction may be made without departing from the spirit of the invention.

We claim:

1. A method for analysis of a fluid flowing in a conduit to determine the presence of low concentrations of salt water and gas in the fluid comprising the steps of:
   (a) bombarding the fluid with fast neutrons, which are slowed down and thereafter engage in thermal neutron capture reactions with materials in the fluid;
   (b) obtaining gamma ray energy spectra of the materials in response to the capture of thermal neutrons by the materials in the fluid;
   (c) obtaining a measure of the concentration of chlorine in the fluid from the gamma ray energy spectra;
   (d) obtaining from the measure of the concentration of chlorine a measure of the concentration of salt water in the fluid;
   (e) obtaining a measure of the concentration of sulfur in the fluid from the gamma ray spectra simultaneously with said step of obtaining a measure of the concentration of chlorine; and
   (f) obtaining from the measure of the concentration of chlorine a measure of the percent gas content of the fluid.

2. The method of claim 1, wherein the fluid is feed stock in a petroleum refining conduit.

3. The method of claim 1, wherein the fluid is refined product in a petroleum refining conduit.

4. The method of claim 1, wherein the fluid is crude oil in a well head conduit at an oil well.

5. The method of claim 1, wherein the fluid is crude oil at a loading dock.

6. The method of claim 1, wherein the fluid is waste water which is to be disposed.

7. The method of claim 1, wherein substantially all the chlorine in the fluid is present as sodium chloride, and wherein the measure of the concentration of salt water is obtained from the measure of the concentration of chlorine.

8. The method of claim 1, wherein said step of obtaining gamma ray energy spectra comprises:
   obtaining gamma ray energy spectra in the range of from 5.0 MeV to 8.0 MeV.

9. The method of claim 8, further including the steps of:
   (a) obtaining gamma ray energy spectra in the range of approximately 2.0 MeV to 2.50 MeV to include the 2.23 MeV capture reaction of hydrogen; and
   (b) using the energy spectra of the 2.23 MeV hydrogen capture reaction as a reference reading for gain stabilization.

10. The method of claim 1, wherein said fast neutrons are emitted from a neutron source and further including the step of:
    attaching said neutron source to the conduit prior to said step of bombarding.

11. The method of claim 1, wherein said fast neutrons are emitted from a neutron source and further including the step of:
    inserting said neutron source into the conduit prior to said step of bombarding.

12. An apparatus for analysis of a fluid flowing in a conduit to determine the presence of low concentrations of salt water and gas in the fluid, comprising:
    (a) means for bombarding the fluid with fast neutrons, which are slowed down and thereafter engage in thermal neutron capture reactions with materials in the fluid;
    (b) means for obtaining gamma ray energy spectra of the materials in response to the capture of the thermal neutrons by the materials in the fluid;
    (c) means for obtaining a measure of the concentration of chlorine in the fluid from the gamma ray energy spectra;
    (d) means for obtaining from the measure of the concentration of chlorine a measure of the concentration of salt water in the fluid; and
    (e) means for obtaining from the measure of the concentration of chlorine a measure of the percent gas content of the fluid.

13. The apparatus of claim 12, wherein said means for bombarding is mounted adjacent a petroleum refining conduit to bombard refinery feed stock and sense the concentration of salt water in feed stock in said conduit.

14. The apparatus of claim 12, wherein said means for bombarding is mounted adjacent a petroleum refining conduit to bombard refinery refined product and sense the concentration of salt water in refined product in said conduit.

15. The apparatus of claim 12, wherein said means for bombarding is mounted adjacent a well head conduit at an oil well to bombard crude oil with neutrons to sense the concentration of salt water in crude oil.

16. The apparatus of claim 12, wherein said means for bombarding is mounted adjacent a conduit at a loading dock to bombard crude oil with neutrons to sense the concentration of salt water in crude oil.

17. The apparatus of claim 12, wherein said means for bombarding is mounted adjacent a conduit to bombard with neutrons waste water to be disposed to sense the concentration of salt water therein.

18. The apparatus of claim 12, wherein said means for obtaining a measure of the concentration of chlorine further includes:
    means for obtaining a measure of the concentration of sulfur in the fluid from the gamma ray spectra simultaneously with a measure of the concentration of chlorine.

19. The apparatus of claim 12, wherein substantially all the chlorine in the fluid is present as sodium chlorine, and wherein the measure of the concentration of salt water is obtained from the measure of the concentration of chlorine.

20. The apparatus of claim 12, wherein said means for obtaining comprises:
    means for obtaining gamma ray energy spectra in the range of from 5.0 MeV to 8.0 MeV.

21. The apparatus of claim 20, further including:
    (a) means for obtaining gamma ray energy spectra in the range of approximately 2.0 MeV to 2.50 MeV to include the 2.23 MeV capture reaction of hydrogen; and
    (b) means for using the energy spectra of the 2.23 MeV hydrogen capture reaction as a reference reading for gain stabilization.

22. The apparatus of claim 12, wherein said means for bombarding is attached to the exterior of said conduit.

23. The apparatus of claim 12, wherein said means for bombarding is inserted into the exterior or said conduit.

* * * * *